United States Patent [19]

Ledford, Jr.

[11] Patent Number: 5,037,611
[45] Date of Patent: Aug. 6, 1991

[54] SAMPLE HANDLING TECHNIQUE

[75] Inventor: Edward B. Ledford, Jr., Lincoln, Nebr.

[73] Assignee: ICR Research Associates, Inc., Lincoln, Nebr.

[21] Appl. No.: 277,679

[22] Filed: Nov. 29, 1988

[51] Int. Cl.$^5$ ............................................. G01N 21/00
[52] U.S. Cl. ...................... 422/63; 250/288; 422/81; 436/171
[58] Field of Search ................. 250/288 R, 288 A; 422/63, 81; 436/48, 171

[56] References Cited

U.S. PATENT DOCUMENTS

| | | | |
|---|---|---|---|
| 3,318,149 | 5/1967 | Varadi | 250/288 A X |
| 4,594,506 | 6/1986 | Ghaderi | 250/288 |
| 4,740,298 | 4/1988 | Anderson et al. | 250/288 A X |
| 4,879,458 | 11/1989 | Brunfeldt et al. | 250/288 |
| 4,908,512 | 3/1990 | Caprioli et al. | 250/288 |

Primary Examiner—Charles Hart
Attorney, Agent, or Firm—Vincent L. Carney

[57] ABSTRACT

To inject samples into a mass spectrometer, one end of a capillary tube is affixed directly to the vacuum chamber of the mass spectrometer or to a mass spectrometer interface to bring gaseous samples into close proximity to the mass spectrometer ionizing means, and the other end is in close proximity to the surface of a tape. The tape is in a cassette and a probe is inserted through the cassette frame between the cassette reels and draws the tape to the end of a capillary tube. Regions of tape with samples adsorbed to tape surface are transported rapidly from a low temperature region for a high temperature region which includes the entrance end of the capillary tube. Sample vaporizes from the tape surface and is carried into the capillary tube by a carrier gas. The tape position is indicated by bar codes on the tape that control tape movement.

27 Claims, 5 Drawing Sheets

SAMPLE HANDLING TECHNIQUE

BACKGROUND OF THE INVENTION

This invention relates to sample injection techniques and more particularly to sample injection for instruments requiring gas or vapor samples such as for example mass spectrometers or gas chromatographs.

One class of sample injector utilizes a moving medium such as a belt or conveyor that carries the samples separated in one instrument into or to another instrument. This class of sample injector is used, for example, to transfer samples from a liquid chromatograph into a mass spectrometer in real time. In these known devices, the samples are caused to adhere to the surface of the belt or conveyor by solvent evaporation and moved into the mass spectrometer where they are subjected to further analysis.

In one type of prior art sample injector of this class, a belt runs from a liquid chromatograph into the high vacuum ionization chamber of a mass spectrometer. The effluent from the outlet of the liquid chromatograph is applied to the belt where it quickly dries and, after being dried, is carried through a series of differentially pumped vacuum locks into the high vacuum ionization chamber of a mass spectrometer for analysis. The sample is then driven off the surface of the belt by heating means or particle bombardment means and ionized in the mass spectrometer source.

These prior art sample injectors have several disadvantages such as: (1) the number of samples analyzed per unit time is limited by the elution rate of a liquid chromatograph; (2) they require movement of an endless or continuous belt from a region of atmospheric pressure to a region of high vacuum; and (3) high levels of operator skill are needed to operate and maintain systems of this type. The above characteristics cause the prior art sample injector techniques to be technically complex and relatively expensive, particularly since they tie up a mass spectrometer while the liquid chromatograph, which is a much less expensive instrument, operates.

SUMMARY OF THE INVENTION

Accordingly, it is an object of the invention to provide a novel sample handling technique.

It is a still further object of the invention to provide an improved technique for coupling a plurality of analytical instruments to a single instrument.

It is a still further object of the invention to provide a novel technique for the injection of samples into an analytical instrument without solvent.

It is a still further object of the invention to provide a novel technique for injecting ions or neutral materials mixed with a carrier gas into an analytical instrument by viscous flow through a capillary tube into the analysis region of instruments which analyze gaseous ions, or gaseous neutral materials.

It is a still further object of the invention to provide an improved technique for analysis of large numbers of samples in times which are short compared to the time required to analyze the same number of samples with the prior art.

It is a still further object of the invention to provide a novel technique for more quickly operating a gas chromatograph.

It is a still further object of the invention to provide a novel technique for coupling different types of instruments to each other.

It is a still further object of the invention to provide a novel technique for preparing sample using a plurality of separation processes at any of several locations and at many different times for fast analysis by a smaller number of analytical instruments.

It is a still further object of the invention to provide a novel method for rapid screening of samples prior to further analysis by an instrument.

It is a still further object of the invention to provide a novel method of selecting certain samples from a plurality of samples taken from a plurality of sources or locations or taken at a plurality of different times for analysis.

In accordance with the above and further objects of the invention, an interface is provided that holds samples for analysis by instruments requiring samples in gaseous form, such as for example mass spectrometry, gas chromatography, flame spectrometry, ion mobility spectrometry, or the like. This interface puts sample into a gaseous or vapor form and moves sample into proximity with an inlet to the instrument or into proximity with an inlet to an analysis section of the instrument.

In one embodiment, the interface includes a movable belt, conveyor or disk. A high temperature heat source, such as a heated probe, is brought into close proximity with the belt, disk or conveyor. When sample material on the belt is moved, by means of belt movement into close proximity to the temperature probe, the high temperature probe rapidly vaporizes the sample and permits the sample, which may also be partially ionized, to be moved by a carrier gas into the instrument.

In another embodiment, the sample is dried on a needle that is part of a needle and stopper combination. The needle is inserted into a hot transfer tube and is thus changed to a vapor or gas for injection by the transfer tube. The stopper is on the needle and forms a seal with the instrument while the needle is coaxially inserted into the transfer tube to permit purging of the instrument with helium to remove air.

In the preferred embodiment, a small transfer tube is affixed with one end in the analysis section of an instrument, such as for example in the vacuum chamber of a mass spectrometer or at a gas inlet thereof, and its other end in proximity to the surface of a cassette tape to move gaseous samples from the tape with a carrier gas such as helium into proximity with the analyzing section of the instrument. For example, the other end of the tube may be within a mass spectrometer ionizing means. Alternatively, the transfer tube may be incorporated into a direct insertion probe and admitted to a high vacuum section of an instrument through an ordinary vacuum lock. Instead of a tape, a rotatable disk may be used in a similar manner.

In other embodiments, the cassette housing is incorporated into a direct insertion probe, evacuated, and inserted into the ionization chamber of a mass spectrometer through an ordinary vacuum lock. The tape is positioned directly in the ionizing chamber in some embodiments by a probe that extends through the cassette housing frame between the cassette reels. In another embodiment, the entire cassette structure is inserted within a mass spectrometer ion source through a suitably designed vacuum lock. In the embodiments in which the tape is within the ionization chamber, samples are driven from the tape surface directly into the ion source either as neutrals or ions without the use of a carrier gas.

The tape may be polyimide, metal, or other high temperature material. The samples may be deposited directly on the tape. In one embodiment, the polyimide tape is bar coded by a laser engraving process and in another embodiment, it has a magnetic coating adapted for recording indicia related to the samples. Portions of the coat are removed to provide a location for samples, and optical indicia that indicate the position of the tape. In another embodiment, laser engraved optical indicia and magnetic recording media are alternated along the length of the same tape or belt.

The tape may be flat or in other embodiments: (1) one or more ridges are fixed proximate to one or more of the edges of the tape and the sample is positioned between the ridges or adjacent to a single ridge to protect the samples from the back of the adjacent winding on a reel and to protect sample from contact with a roller and capstan drive; (2) adsorbant media may be affixed to the tape and the sample imparted to them; (3) sample may be combined with an easily vaporizable matrix material to enhance volatilization of otherwise nonvolatile or thermolabile samples; or (4) the region of the tape to which the sample is imparted may be perforated to permit flow of gas or light through the sample containing region, and further to permit easy and uniform deposition of samples carried by a solvent which will adhere by surface tension to the perforated area of the tape.

In still another embodiment, a needle has a stopper around its shank. The needle may receive dried sample on its tip and be inserted into the heated transfer tube with the stopper sealing the transfer tube so as to pressurize it and establish an appropriate flow of carrier gas. The needle may be retractable into a sheath, so that the sheath and needle are inserted in a transfer tube and the sample evaporated in the transfer tube when the needle is pushed forward out of the sheath.

In use, a cassette is used for coupling different analytical instruments to each other to provide successive stages of analysis even though the instruments are remote from one another and operate at different speeds. Moreover, several instruments may supply one fast instrument, such as for example, several gas or liquid chromatographs, supplying one mass spectrometer.

In one mode of use, samples are gathered from a number of sources and deposited on tape, wire or disks. For example, a crude sample can be gathered in the field, and extracted. Extract carrying sample material may be deposited on tape within cassettes. These cassettes may be transported to a laboratory where samples may be further analyzed or further separated into components, and some of the components may be deposited on cassettes for still further analysis. In all of the operation, the natural speed of instruments is utilized because the cassette can be used at the speed of the instrument which deposits sample onto the cassette tape or draws sample from the cassette tape. In particular, when the cassette is used to supply a gas chromatograph, it provides unusual speed of operation because the sample is vaporized with exceptional speed. Sharp injection permits the gas chromatograph to be operated with short columns and high carrier gas flow rates which result in a high rate of analysis.

Gaseous ions have been shown to be transmissible through the transfer tube so that the assembly may also be used as an ion source if ionizing means are used to ionize the sample prior to or during its passage through the transfer tube.

From the above description, it can be understood that the sample injection technique of this invention has several advantages such as: (1) it is economical in construction; (2) it can provide for rapid, sequential and automatic sample injection to a mass spectrometer or ion mobility spectrometer of stored samples from a slower source such as a liquid chromatograph; (3) it is adaptable to be used with gas chromatographs to provide sharper peaks and faster operation by supplying the samples rapidly in gaseous form to the gas chromatograph; (4) it can be used to collect samples from a gas chromatograph since gas chromatographic effluents have been shown to condense upon the surface of the tape if the latter is held in proximity to the exit of the gas chromatographic column and maintained at room temperature; (5) it can be operated at atmospheric pressure or at other pressures in the regime of viscous flow and at room temperature thus providing for superior economical operation; and (6) when combined with appropriate ionizing means and transfer tube geometry, it may be used as an ion source.

SUMMARY OF THE DRAWINGS

The above noted and other features of the invention will be better understood from the following detailed description when considered with reference to the accompanying drawings in which.

DETAILED DESCRIPTION

Figure 1:
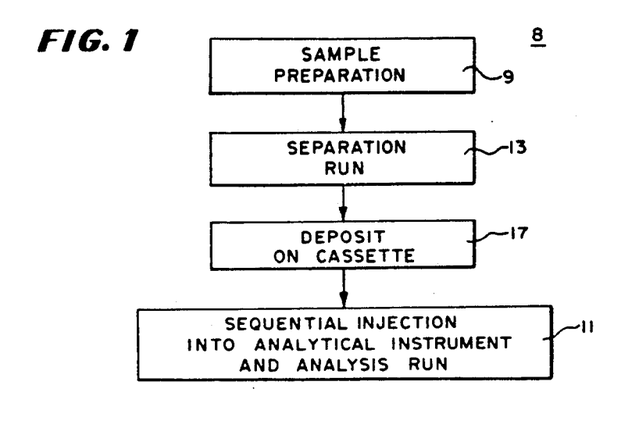
FIG. 1 is a block diagram illustrating the technique of this invention.

In FIG. 1, there is shown a block diagram 8 illustrating a process for using a sample injector in accordance with the invention and comprising the step of the sample preparation 9, the step 13 of making a separation run such as with liquid chromatography, gas chromatography solid phase extraction, immunoprecipitation, liquid/liquid extraction, or other separation means, the step 17 of depositing the separated components onto a cassette, and the step 11 of sequential sample injection into an instrument such as for example a mass spectrometer, a gas chromatograph, a flame spectrometer or an ion mobility spectrometer or the like and making an analysis run after the sample injection into the instrument.

The step 9 of preparing the sample may comprise conventional or novel steps used to prepare a sample for the process selected to be performed in the step 13 of separating the components of the sample in a run by an instrument in the separation sciences such as liquid chromatography. The steps of preparing the sample and making the run may in themselves be inventive, but are only used as part of the process related to the invention and any standard process may also be used.

The step 17 of depositing separated components of the samples, such as peaks in the effluent from a liquid or gas chromatograph, in series to a high-temperature, inert, flexible tape may be accomplished by any suitable method. The order of the samples may be the order in which they are eluted from the liquid or gas chromatographic column, to form a series of spots on the tape as the tape is moved and, in the case of liquid chromatography, solvent evaporates to cause drying of the sample.

This tape is wound on reels and is used in conjunction with the step 11 of sequential injection into the analytical instrument and analysis run. In the process of causing the sample to be deposited on the tape, a portion of the sample may be transmitted through a detector of any suitable type suitable to determine the purity and/or quantity of the sample. This step can be used to prepare a record of the sample so that if it is not pure, a mixed sample analysis may be performed or further steps may be taken to purify it before analyzing it in the mass spectrometer or other instrument.

While FIG. 1 illustrates one sequence including the steps of separating components and depositing them on a tape, actually several may be used in sequence. For example, samples of material containing pesticides may be obtained and a simple separation of a sample from the material made in the field by injecting the material into the top of a packing of a simple portable column, applying an appropriate solvent, applying the resulting effluent to a tape, permitting evaporation of the solvent and marking the location on the tape with an identification of the field location to obtain a compact cassette of samples. The cassette of samples may be transported to a remote facility. The samples may then be separated into components by gas chromatography by evaporating each sample from the tape and making a chromatographic run and the components viewed on a detector as they are eluted. The suitable components may be deposited on-line on another tape to prepare another cassette for further analysis such as in step 11 of the process.

In the preferred embodiment, the step 11 of injecting the sample into the mass spectrometer comprises the step of inserting a cassette into a cassette holder near the sample inlet to the mass spectrometer against the flow of an inert gas that sweeps the holder free of oxygen and gently lowers the cassette. The gas is at a first relatively high pressure. The cassette has two reels, one of which has the tape with samples on it and the other of which is empty and about to receive the portion of the tape having the samples.

After this cassette is inserted into the cassette holder, the cassette holder is sealed and the cassette reels connected to a mechanism for turning the reels while a carrier gas, such as helium, flows through the cassette and around the reel to avoid the introduction of oxygen into the mass spectrometer. This gas is at a second pressure lower than the first pressure. The samples are injected without solvent and flow through a transfer tube in the preferred embodiment by viscous flow in which the mean free path between gaseous particles, which may be neutrals or ions, is small compared to the diameter of the transfer tube.

To remove the sample from the tape and insert it into the transfer tube, the tape is normally positioned with the heated tip contacting a portion of the tape between samples. The portion of the tape containing sample is then moved quickly to the heated tip. Samples evaporates rapidly, and is carried down a transfer tube by carrier gas flow. Following sample evaporation and analysis, the heater probe is retracted, the tape is again moved to a location between samples, and the heater probe again brought into contact with the tape. The heated tip is at a temperature of between 300 and 450 degrees Centigrade and provides rapid vaporization of samples within a time substantially less than one second. This vapor may be transferred to an ionizing means for analysis in a mass spectrometer.

Alternatively, a probe may be used to push a strand of the tape containing the samples into a vacuum chamber and in proximity to the ionization chamber. The probe has a provision for heating the tape but only at its tip and the cassette is maintained at or about room temperature to avoid the temperature of the cassette from being elevated to the point that sample is caused to evaporate on the tape while it is still wound on reels within the cassette. With this arrangement, it is possible to move the tape containing samples across the tip of the probe within the ionization chamber while the probe is heated.

The sample then is subjected to a mass spectrographic run. This may be done using any type of mass spectrometer. This injection and analysis may also be done with any analytical instrument adapted to receive samples in gaseous phase. For example, if the sample is to be injected into a gas chromatograph instead of a mass spectrometer, the injection is accomplished in a manner similar to the injection into a mass spectrometer. The transfer tube delivers sample to a gas chromatographic column instead of a vacuum chamber. In particular, samples collected at the output of one gas chromatograph may be admitted to a second gas chromatograph equipped with a different type of column, effecting high speed two dimensional gas chromatography.

The step of making a gas chromatographic run may be done in a novel manner after the sample is injected. Because of the fast evaporation of the sample using the sample injection technique of step 11, sharp peaks can be formed in the gas chromatograph and a much faster run may be made such as in the order of 1/100th or less of the time of a gas chromatographic run using a conventional sample injector, septum and vaporizer.

To remove the cassette, the gas pressure in the cassette holder is increased and the vacuum lock opened. The pressure when inserting and removing the cassette is in the range of 2 to 10 pounds per square inch and the pressure during operation is in the range of 0.1 to 10 pounds per square inch. However, the pressures differ depending on the spaces in the cassette holder and the cassette, on the weight of the cassette and upon the gas load delivered to the analytical instrument. The optimum pressures can be determined experimentally.

Instead of drying the sample on a tape, sample may be dried on a disk. The samples are rotated on the disk into proximity with the transfer tube inlet and heated to vaporize the sample. Moreover, the sample may be evaporated onto a thin wire having a stopper affixed to it. The sample is thrust with the wire into a transfer tube with the stopper closing the inlet to permit pressurization of the transfer tube and the transfer tube is continually swept by a helium carrier to prevent air diffusion. The sample is evaporated by the transfer tube and carried by viscous flow through the transfer tube. In any of the above embodiments, sample may be first ionized such as by a radioactive source or laser ionization or thermal shock heating and then ions transferred by a transfer tube of suitable geometry using viscous flow. In the alternative, the carrier gas may be mixed with a reagent gas in a manner known in the art so as to achieve chemical ionization of sample molecules within the transfer tube.

Figure 2:
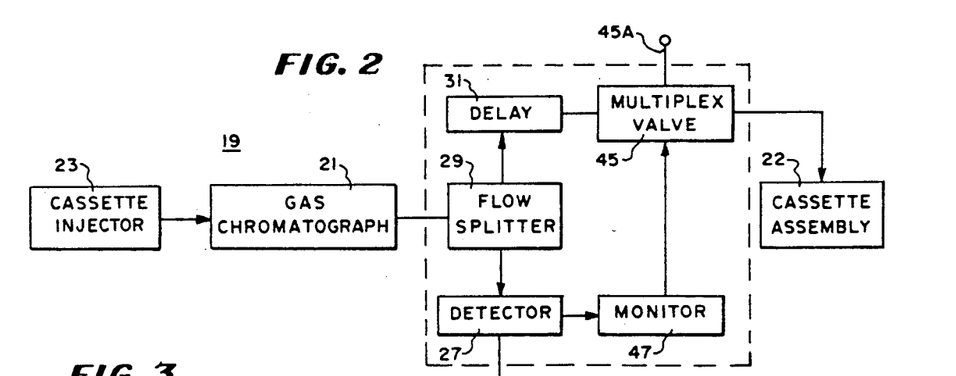
FIG. 2 is a block diagram of an apparatus for applying samples to a tape for storage.

In FIG. 2, there is shown a schematic diagram of an apparatus 19 for preparing samples on a sample tape, which apparatus includes a sample injector such as a cassette injector 23, a separating apparatus such as a gas chromatograph 21, a peak selector 25 and apparatus for depositing samples on tape for further analysis. The sample injector rapidly injects samples into the separating means and the separated components are viewed and some selected for saving on a tape by the sample selector.

In the preferred embodiment, the samples are injected using the method of FIG. 1. They may be injected into any separating apparatus which employs gas phase separation, such as a gas chromatograph or into other types of separating apparatus via a suitable interface. However, special advantages are obtained from the combination of the cassette injection technique of FIG. 1 and a gas chromatograph. It has been found that the cassette injection technique of FIG. 1 carries samples rapidly into the gas chromatograph, resulting in surprisingly sharp peaks and resulting in increased speed of processing. Although a cassette injector 23 is preferred, other sample injection techniques such as with a needle and stopper combination, or a rotating disk, may be used to achieve the advantage of sharp injection.

To select particular peaks, the peak selector 25 includes a flow splitter 29, a delay 31, a detector 27, a multiplex valve 45 and a monitor 47. The flow splitter 29 is mounted at the end of the gas chromatograph 21 and channels some effluent to the detector 27 and some of the effluent to the delay 31. The delay 31 may be a length of capillary tube and applies the sample to a multiplex valve 45 that either exhausts effluent or supplies effluent to the tape in cassette assembly 22 under the control of the monitor 47 which uses information obtained from the detector 27 to select peaks for application to the tape in the cassette assembly 22.

The flow splitter may include two channels with the smaller channel being connected to the detector and the larger to the delay 31 or vice versa, or a fast rotary or fluidic valve which is periodically switched to one position to provide a flow of effluent to a detector 27 through a conduit or in the alternative to cause a flow to the delay 31.

The sample outlet from the peak selector 25 is positioned approximately 2 millimeters from the tape in the cassette assembly 22. The tape is maintained at room temperature, and the sample condenses on the tape leaving small spots of sample. The unselected sample is exhausted through an exhaust line 45A. The monitor 47 may be a display so that a user can manually select peaks by actuating the multiplex valve 45 or this operation may be computerized to detect peaks by characteristics such as amplitude. width, retention time, or other criteria and combinations of criteria. The detector 27 may be any appropriate detector such as a flame ionization, electron capture, ion mobility detector, or other detector which detects gaseous vapors in a manner known in the art.

In operation, sample is injected into the separation apparatus such as the gas chromatograph 21 and separated or partially separated into components. The separated or partially separated components in the effluent of the gas chromatograph 21 is split with one portion flowing to a detector 27 and the other through a delay line to the multiplex valve 45.

The sample, after being detected, may be applied to the tape in the cassette assembly 22. To accomplish this, the tape cassette assembly 22 is mounted in a cassette on reels. =he outlet from the multiplex valve 45 is brought through a heated transfer line to an opening in the cassette housing which permits the effluent emerging from the transfer line to be applied to the surface of the tape in the cassette assembly 22. The tape may be stationary during deposition or may be moved.

Figure 3:
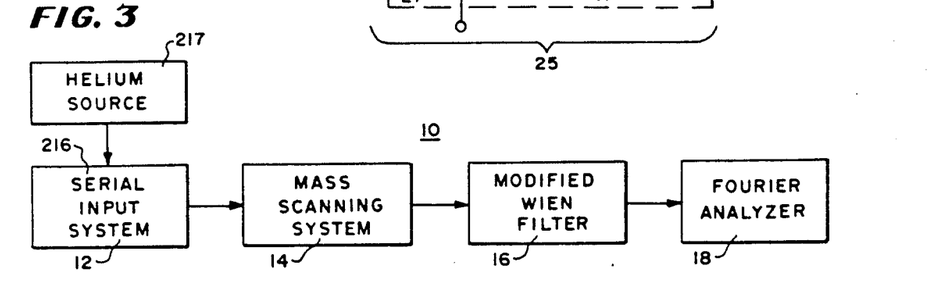
FIG. 3 is a block diagram of a spectrometer using a sample injection technique in accordance with an embodiment of the invention.

In FIG. 3, there is disclosed a mass spectrometer 10 having a serial input system 12, a mass scanning system 14, a modified Wien filter 16 and a Fourier analyzer 18. The serial input system 12 feeds samples rapidly to the mass scanning system 14 which, one after the other, ionizes and resolves the constituents of the sample and applies the resolved ions to the modified Wien filter 16. The modified Wien filter 16 takes each of the resolved components and further resolves them, applying the result to the Fourier analyzer 18 to obtain a readout of the components supplied to the modified Wien filter 16.

The mass scanning system 14 is a mass selective source of ions maintained at a potential suitably related to the modified Wien filter 16 to permit injection of a beam of ions from the mass scanning system 14 into the modified Wien filter 16.

Figure 4:
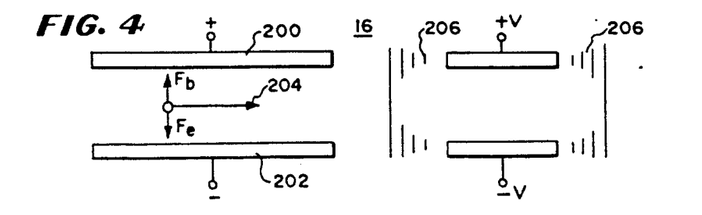
FIG. 4 is a schematic drawing of a modified Wien filter used in the system of FIG. 3.

In FIG. 4, there is shown a side schematic view of the modified Wien filter 16, described in connection with FIG. 3, having first and second conductive plates 200 and 202 parallel to each other and having opposite DC potentials applied to them so as to create an electric force transverse to the Wien filter longitudinal axis on an ion 204 injected between them. A magnetic field is applied perpendicular to the electric field to exert a force of equal magnitude but of opposite direction to the force exerted by the transverse electric field so the ion travels without being deflected in the transverse direction. Certain thin end plates 206 are utilized to neutralize the electrostatic lens effect, as described in the publication by Lars Wahlin, "The Colutron, a Zero Deflection Isotope Separator", Nuclear Inst. and Method, 27, 1964, p. 55–60, North-Hol land Publishing Co., and secondarily to restrain ion motion in a direction parallel to the magnetic field by means of appropriate voltage biases applied to the thin plates.

While the ions are traveling between the plates, the differential voltage on plates 200 and 202 is suddenly disconnected to eliminate the transverse electric field, leaving only the magnetic field and such electrostatic trapping field as may be necessary to confine ions along the direction of the magnetic field. This causes each of the ions to orbit and electrostatically induce signals upon plates 200 and 202 which signals can be detected by amplification means incorporated into the Fourier analyzer 18 (FIG. 3) to indicate the mass of the ion.

Figure 5:
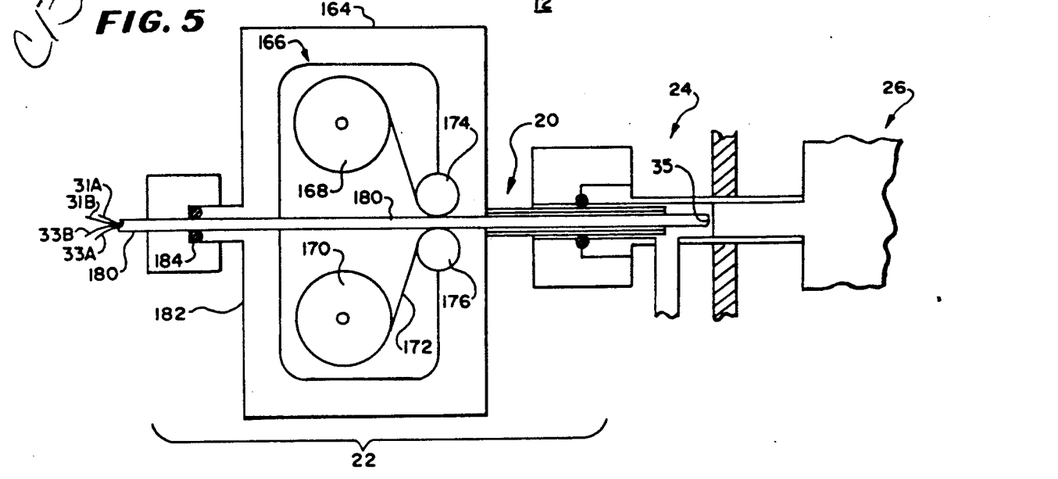
FIG. 5 is a schematic diagram showing a sample injector in accordance with the invention coupled through a vacuum lock for the transfer of samples to the ion source of a mass spectrometer.

In FIG. 5, there is shown a schematic diagram of a serial input system 12 having a probe assembly 20, a cassette assembly 22, a sample vaporizing assembly 24 and a mass spectrometer ion source 26. The cassette assembly 22 includes a cassette having a tape wound upon its reels 168 and 170 with sequentially deposited samples on the tape, each of which receives heat from the vaporizing assembly 24 in sequence to vaporize it. The heat sends gaseous sample through the mass spectrometer ion source 26.

The probe assembly 20 includes an elongated probe 180, a vacuum housing 182 and seals 184. The vacuum housing 182 communicates with the cassette assembly 166 and the elongated probe 180 passes through the two and includes a conductor pair 31A and 31B for applying power to an electrical heating element and a conductor pair 33A and 33B for measuring the temperature in the tip 35 of the elongated probe 180.

The cassette assembly 22 includes a cassette housing 164, a cassette 166, seals 184, and heater assembly 24. The cassette 166 includes first and second reels 168 and 170, respectively, rotatably mounted in the cassette housing 164 and adapted to hold a tape or belt or other flexible member 172 and first and second rollers 174 and 176 for guiding the motion of the belt 166 and of such construction as not to contact samples affixed thereto. The reels 168 and 170 are spaced from each other to permit a mechanical probe to pass between them and the rollers 174 and 176 are mounted on opposite sides of the probe to hold the belt 166 about the probe. The cassette assembly 22 accommodates a probe that can be inserted through the cassette frame and between the reels so that the tape may be drawn forward by the probe. This permits the tape to be inserted into a mass spectrometer ion source or other vacuum chamber, into a solvent bath, or into tubes and chambers where special chemical and/or deposition processes may take place or to a location adjacent to a transfer tube to be described hereinafter as one embodiment within the mass spectrometer ion source 26.

Figure 6:
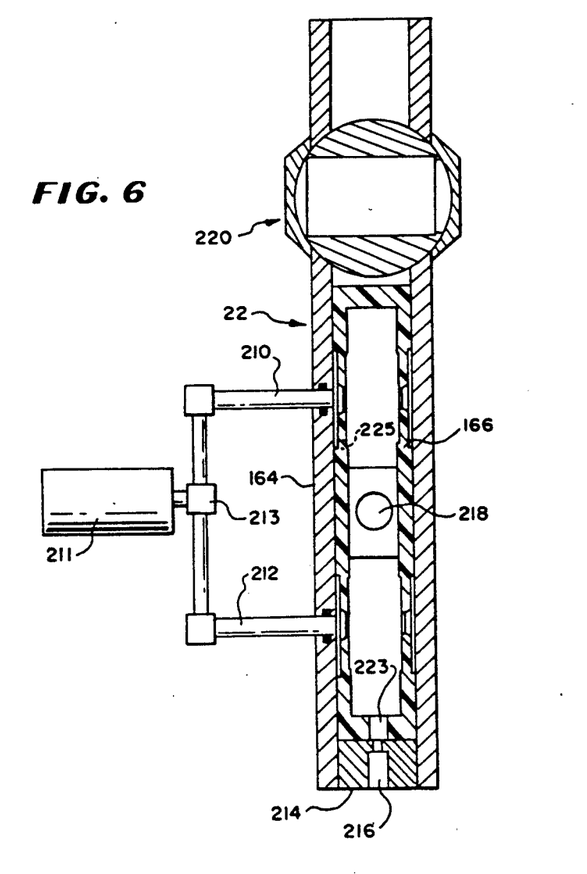
FIG. 6 is a view of a cassette holder used in an embodiment of the invention.

In FIG. 6, there is shown a cassette holder 22, having a housing 164, with a cassette 166 within it engaging first and second drive shafts 210 and 212 connected to a movable assembly and driven by a drive motor 211 through a transmission 213 for driving the reels of the cassette 166. The housing 164 is generally aluminum adapted to receive a nozzle at 216 for the application of helium. In the alternative, two motors may be mounted to a retractable support, with each motor driving a shaft for a different reel.

To prevent air from entering the instrument, the cassette 166 fits relatively tightly so that the helium tends to buffer it within the housing 164 but permits engagement of the drive shafts 210 and 212 to establish a driving relationship with the reels therein. The tolerances are closer than 15 thousandths of an inch and in the preferred embodiment are 5 to 10 thousandths. This permits the oxygen from air to be swept from the housing 164 as the cassette 166 is dropped against a pressure in the range of 2 to 10 pounds per square inch. To further avoid back-diffusion of air during operation, a pressure in the range of 0.1 to 10 pounds per square inch is applied interior to the cassette housing.

To insert the tape into the mass spectrometer ion source, a horizontal central aperture 218 is provided through which a probe may be inserted between the reels of the cassette. An air lock 220 in the upper portion of the cassette holder may be turned in one position to permit a cassette to be dropped into the holder and in the other position to provide an airtight seal.

Figure 7:
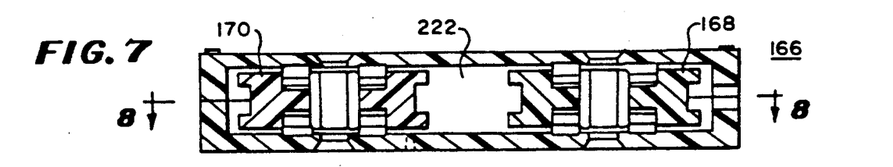
FIG. 7 is a sectional view of a suitable cassette for use in the cassette holder of FIG. 6.

In FIG. 7, there is shown a sectional view of a suitable cassette 166 without the tape wound around the reels. As shown in this figure, the cassette includes two reels 168 and 170 adapted to receive a polyimide tape. An open space 222 is provided between the reels through which a probe may extend.

Figure 8:
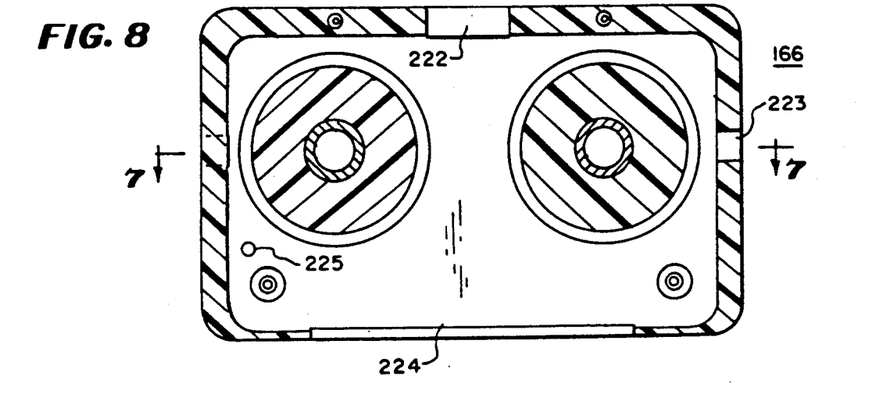
FIG. 8 is a sectional view taken through section lines 8—8 of FIG. 7.

In FIG. 8, there is shown a sectional view of the cassette 166 taken through section lines 10—10 of FIG. 7 illustrating the opening 222 on one side of the housing and a corresponding but wider opening 224 on the other side to permit the extension of a probe. With that mechanism, the probe can move the tape adjacent to the capillary tube section where the tape may be moved about the heated tip to provide for vaporization of samples.

To permit gas to sweep the oxygen from the cassette and to aid in the ejection of the cassette 166 from the cassette holder, the casing includes a first opening 223 in a bottom edge of the cassette which, in the preferred embodiment, is aligned with the gas inlet 216 to the cassette holder 22 (FIG. 6) and a second smaller opening 225 in the side of the cassette 166 to permit the escape of gas from the cassette 166. This enables the cassette 166 to slowly be inserted and to be ejected partly until the opening 225 permits enough escape of gas to halt the upward lifting of the cassette 166. The opening 225 is approximately one-sixteenth of an inch in diameter in the preferred embodiment.

Figure 9:
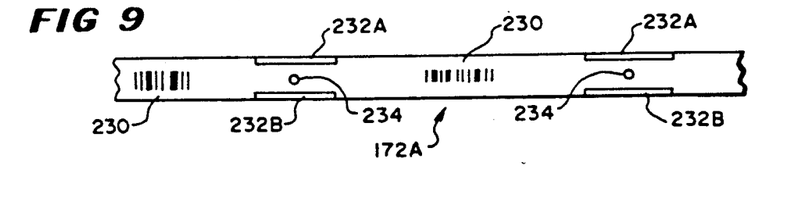
FIG. 9 is a top view of a small section of tape used in the cassette of FIG. 7.

In FIG. 9, there is shown a top view of a small section of tape 172A having a plurality of optical markers 230, side raised tape portions 232A and 232B, and a plurality of sample areas 234 which may or may not be perforated. The optical markers provide identification and position information for the sample areas 234.

Figure 10:
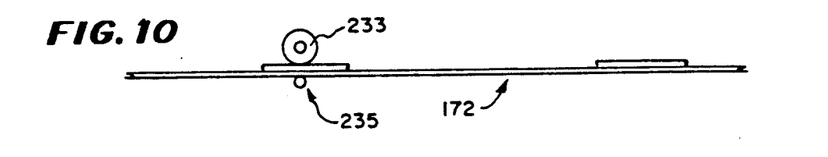
FIG. 10 is a side view of a section of tape of FIG. 9.

In FIG. 10, there is shown a side view of the section of tape of FIG. 9 showing the manner in which the side portions are raised to protect the sample spaced in between them and to permit the contact of the rails by a spring-loaded drive roller 233 and capstan 235 for movement thereof. The side portions may be continuous or intermittant but should at least be located on the sides of the sample 234.

Figure 11:
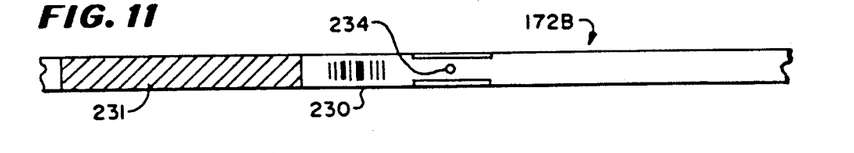
FIG. 11 is a fragmentary plan view of a section of another embodiment of tape.

FIG. 11 is a fragmentary top view of a section of another embodiment of tape 172B, having optical markers 230 and magnetic recording medium 231 for recording indexing and other information concerning the sample.

Figure 12:
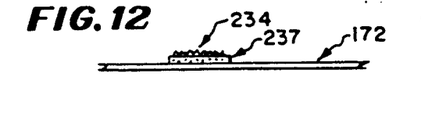
FIG. 12 is a fragmentary side elevational view of the section of tape shown in FIG. 11.

In the side view of FIG. 12, the sample 234 is deposited on an adsorbant material 237. The sample will vaporize out of the high temperature adsorbant material when the back of the tape 172 is heated.

Figure 13:
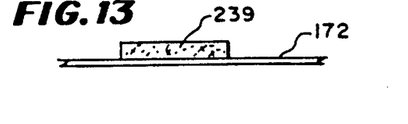
FIG. 13 is a fragmentary side elevational view of still another embodiment of tape.

In the case of a sample which is not sufficiently volatile to vaporize, it may be embedded in an explosive or decomposable material, or material which will undergo a phase explosion upon rapid heating, to cause the nonvolatile sample to be gasified, suitable for analysis in a mass spectrometer. A combination of explosive material and sample is shown at 239 in FIG. 13 on tape 172.

Figure 14:
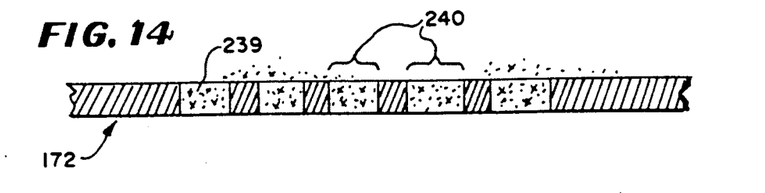
FIG. 14 is a plan view of another embodiment of tape.

In FIG. 14, there is shown a sectional view of the sample containing region of the tape 172 carrying perforations or through holes 240 as might be created with a laser drilling process. Sample combined with a gasifiable matrix 239 is dried in and around and upon the walls of the perforations, which permit simultaneous passage of carrier gas and electromagnetic radiation such as may vaporize the gasifiable matrix and in addition may partially ionize the gaseous vapors so produced.

Figure 15:
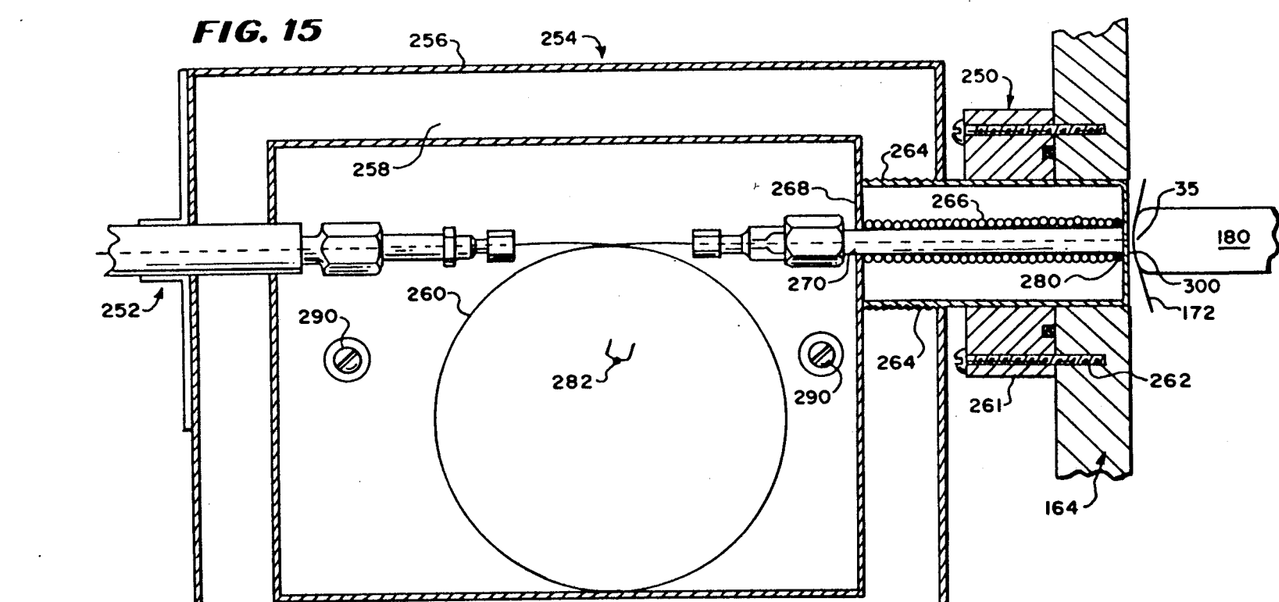
FIG. 15 is a schematic side view of a mass spectrometer interface useful in the embodiment of FIG. 3.

In FIG. 15, there is shown a fragmentary schematic side view of a portion of a mass spectrometer interface within the serial input system 12 (FIG. 3) having a transfer-tube sample-vaporizer coupling assembly 250, a temperature control container 254, and an ionization-chamber transfer-tube coupling assembly 252. A capillary tube 260 is carried by the transfer-tube sample-vaporizer coupling assembly 250, a temperature control container 254, and an ionization-chamber transfer-tube coupling assembly 252 from the inlet end of a transfer line extending from the mass spectrometer to the ionization-chamber transfer-tube coupling assembly 252. Sample from the tape 172 is transported via the transfer tube-sample vaporizer coupling assembly 250 and the capillary 260 to the ionization chamber transfer-tube coupling assembly, thence to the ionization chamber of a mass spectrometer. Alternatively, sample may be transported into the analyzing section of another instrument.

The transfer-tube sample-vaporizer coupling assembly 250 brings transfer-tube 302 into proximity to tape 172 in contact with the end 35 of the probe 180 so that when a sample is heated and vaporized, it is moved into the transfer tube for transference to the ion chamber of the mass spectrometer. With this arrangement, the end of the heated probe 35 is positioned within 5 thousandths of an inch of the transfer-tube sample-vaporizer coupling assembly 250 so that the vaporized sample will enter a central conduit thereof and be transferred without blockage or deposition caused by cooling, to the ionization chamber of the mass spectrometer. The sample is received at the capillary tube 260 which is adheared to an end surface of the transfer-tube sample-vaporizer coupling assembly 250.

To mount the transfer tube to the cassette housing wall, the transfer-tube sample-vaporizer coupling assembly 250 includes a bracket 261 adapted to receive bolts or other fasteners, one of which is shown at 262 and receives in a central opening with a press fit the capillary-holding sleeve or outer cylindrical tubular shell 264. With this arrangement, the capillary-holding sleeve 264 is mounted to the cassette housing wall such that the input end of the sample transfer tube is adjacent to the tape 172.

Within the capillary-holding sleeve 264, there is an insulator 268 which may be an air space, and a central inner heating tube 270 with heating coils 266 outside of it and a central elongated capillary tube through which vapor is transferred. Between the insulator 268 and the central inner heating tubing 270 are heating coils 266 thermostatically controlled to maintain the temperature of the central inner heating tube 270 at the proper temperature. The end of the central inner heating tube 270 enters the temperature control container 254 where it receives the extending capillary tube 260, which is looped in the heating compartment and extends at its other end within the temperature control container 254 to the ionization chamber transfer-tube coupling assembly 252.

To maintain the temperature of the vaporized sample constant and prevent it from condensing within the capillary tube 260, the temperature control container 254 includes an outer metallic hollow shell 256 formed as a right regular parallelopiped and having an internal insulating layer 258 defining within it a right regular parallelopiped opening for containing the capillary tube 260 and the ends of the couplers. This box is openable at one end and may be mounted to a surface outside of the mass spectrometer by bolts or screws or the like indicated at 290. The central inner heating tube 270 and the compartment are thermostatically controlled by the temperature sensors 280 and 282.

The length of the capillary tube 260 in the preferred embodiment is approximately 30 centimeters and its inner diameter is approximately 0.25 millimeter. However, it may be between 5 and 30 centimeters and have a diameter of between 0.001 and 0.010 inches. The capillary tube 260 draws this gas load from helium gas supplied to the cassette chamber through the gas entrance port. The pressure difference that draws the gas need not be with respect to atmosphere but only needs to cause the helium or other gas to sweep the sample into the transfer tube.

Figure 16:
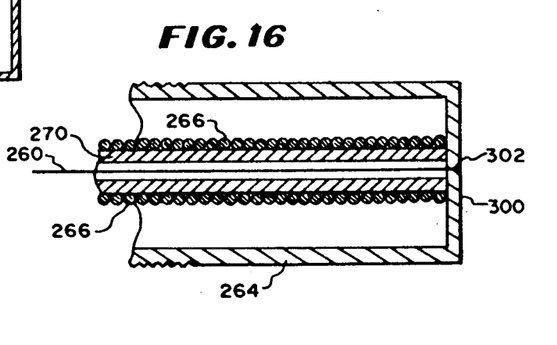
FIG. 16 is an enlarged, fragmentary, longitudinally sectioned view of a coupling sleeve and capillary tube useful in the embodiment of FIG. 3.

In FIG. 16, there is shown an enlarged, fragmentary, longitudinally sectioned view of the capillary holding sleeve 264, central inner heating tube 270 and capillary tube 260, with the capillary holding sleeve 264 having a diameter of approximately 0.1 inches, the central inner heating tube 270 being coaxial with the capillary holding sleeve 264, and the capillary tube 260 being coaxial with the inner tube. The capillary holding sleeve 264 is stainless steel and a moderate conductor of heat. The central inner heating tube 270 is brass or copper and a good conductor. It includes heating wires around it and because it is a good heat conductor maintains the capillary tube 260 within it and the face 300 of the assembly nearest the tape at the desired temperature without heating the outer sleeve to such an extent that heat is conducted to the cassette (not shown in FIG. 15). Capillary tube 260 is mounted along the central longitudinal axis of the capillary holding sleeve 264, and sealed at the face 300 of the assembly. The face 300 is relatively thin such as approximately 0.060 inch so that sample enters the heated capillary without a long path through face 300.

The brass central inner heating tube 270 is cylindrical in the preferred embodiment and formed of a good heat conducting material, having an insulated Nicrome wire heating element 266 wound around it for temperature control. An axially extending longitudinal axis matches with a small aperture in one end (the face) 300 of the capillary holding sleeve 264 which receives the transfer tube capillary 260. At this junction, a 0.25 millimeter inner diameter deactivated fused silica capillary tube 260 communicates with the end of the cylindrical opening 302 with its outer wall sealed against the inside of the cylindrical opening 302 so that the capillary tube 260, receives the entire sample. The capillary tube 260 extends through the coupler and into the temperature control container 254 (FIG. 15) and into the ionization-chamber transfer-tube coupling assembly 252, for deposition of a vaporized sample therein, and subsequent transport by carrier gas to the mass spectrometer ionizing chamber.

Figure 17:
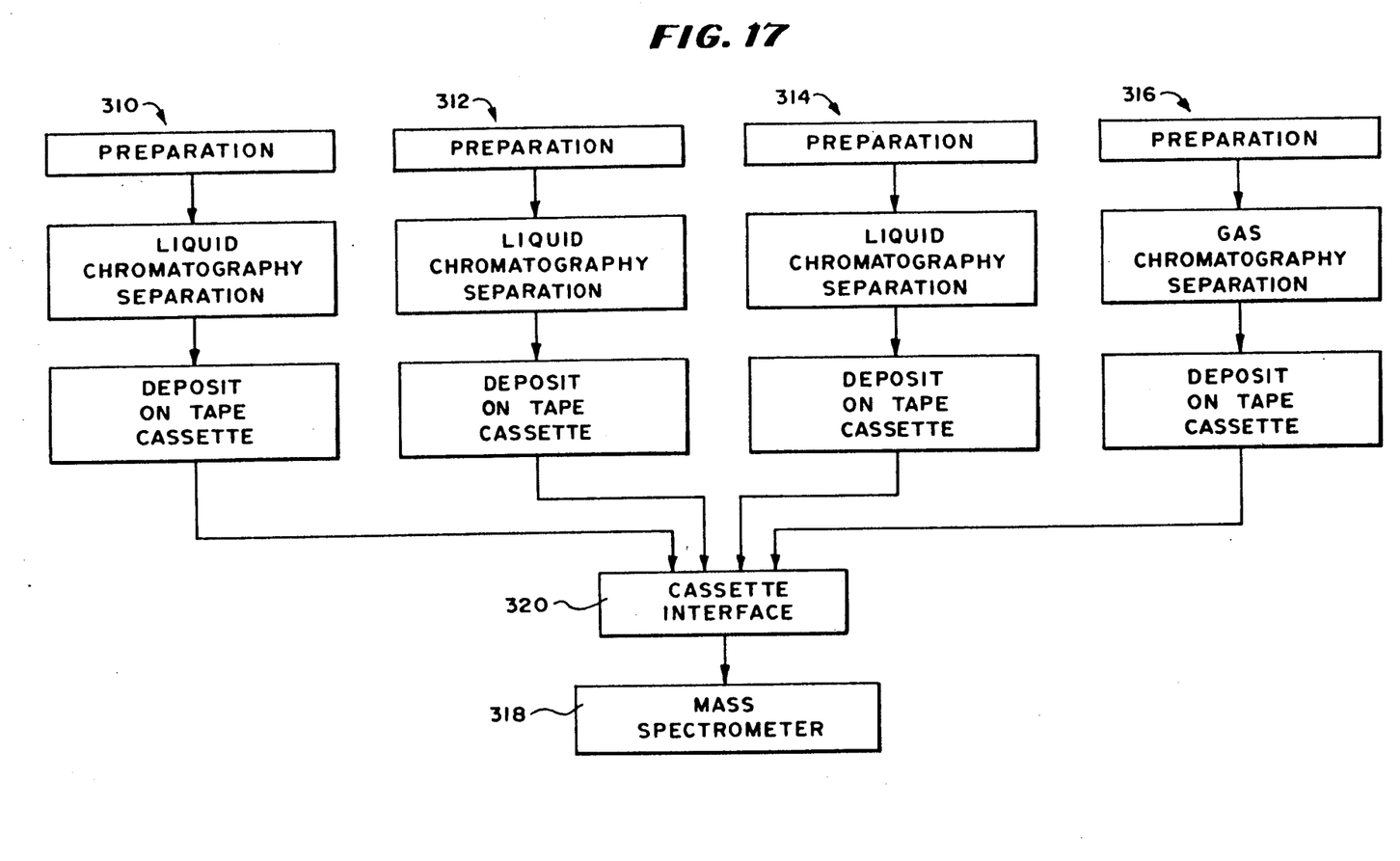
FIG. 17 is a block diagram of one method showing the use of an apparatus for injecting samples into an instrument according to an embodiment of the invention.

In FIG. 17, there is shown a block diagram illustrating the operation of the coupling technique of the invention having a plurality of sources of sample such as samples from liquid chromatography 310, 312 and 314 and samples from gas chromatography 316. These samples may be of materials such as environmental samples or other organic materials used in medicine and may be from the same or different sources. The same starting sample may be analyzed by more than one technique such as liquid and gas chromatography and put on different cassettes and than analyzed in the mass spectrometer 318 using the cassette interface 320.

With this arrangement, cassettes may be inserted and indexed to a set of peaks and analyzed in the mass spectrometer so that similar materials obtained by different methods or in different runs can be run in sequence in the mass spectrometer 318 even though other samples have been collected on the cassettes which serve as sample collectors.

Moreover, the cassettes can be run in any order or may be accummulated in any manner to increase the speed and efficiency of the throughput of the mass spectrometer. Thus samples may be collected by a number of different originating sources and sent to a central source for mass spectrometer analysis.

In operation, low temperatures in the capillary tube 260 produce sluggish response since "volatile" materials adsorb to surfaces if the temperatures of the latter are too low. The temperature range may be between 200 and 400 degrees Centigrade but the preferred range at the tape and capillary tube interface is 275 degrees Centigrade to 325 degrees Centigrade.

To monitor the temperature, thermocouples are mounted in close proximity to the heated tape surface, and to the entrance of the capillary tube.

To prevent the entire cassette housing and cassette tape within it from being heated to the extent that the sample is vaporized in an uncontrolled way when the capillary tube and cartridge heater are operated, thermal insulation of the heated elements from the body of the cassette structure is used. Only short, localized regions of the cassette tape are heated at a given moment.

All entrances to the cassette tape chamber are sealed to prevent diffusion of air into the chamber, and consequent delivery of oxygen to the mass spectrometer. Room temperature entrances are O-ring sealed. The high temperature entrances can be sealed with high temperature adhesives, coatings, potting compounds, etc. Thermal insulation barriers between heated entrances and their associated gas seals is desirable.

It is necessary to operate the cassette chamber with oxygen free gas, e.g., helium, to prevent diffusion of air into the cassette housing and mass spectrometer, and to supply the gas load delivered by the capillary tube. This is readily accomplished by sweeping helium gas continuously through the cassette chamber. If the cassette is operated at a positive pressure, excess helium gas from the chamber should be exhausted to atmosphere from the chamber through a narrow orifice or tube, such that the linear velocity of the flow through the tube at a mass flow rate of roughly std. 10 cc/minute is greater than the diffusion velocity of air through the exhaust tube. Otherwise air will back-diffuse up the exhaust tube and into the cassette chamber.

Unwanted air is rapidly swept away with a high rate of helium flow. The closer the helium entrance tube is to the sampling gap, the more effective the purge of air. Helium purge in the preferred embodiment is provided using solenoid operated valves to open $\frac{1}{8}$-inch diameter tubes through which high Helium flow rates can be maintained. Immediately after inserting a new cassette, the chamber is purged for a few seconds to remove air from the cassette structure.

Tape speeds of several inches per second are used for transporting samples to the heater. Sudden stoppage of the tape is necessary to position samples over the heater. Gradual approach of the sample to the heater is not desirable. Rewind capability is desirable. Stepper motors may be used to drive the reels, however, in embodiments emplying direct drive of the tape reels (rather than capstan drive of the tape itself) the relation between motor spindle position and linear displacement along the tape length is complicated by the varying diameter of the tape windings. A simple motor with a brake or clutch is adequate.

Bare Kapton, (trademark of Du Pont de Nemours, E.I. & Co., Wilmington, Delaware 19898, U.S.A.) polyimide film 1 to 5 mil thick, which is the material used in commercial LCMS belt interfaces, is used as the tape. Samples are deposited on bare Kapton. An intermittent magnetic coating on a Kapton base provides for the recording of data. This can be prepared by stripping the magnetic coat of high temperature flight recording tape with tetrahydrofuran to remove the recording medium and form sample locations between recording locations. By dissolving the coating periodically along the tape, alternating Bare Kapton and recording regions can be set up. This also has the advantage that photo-interrupters can be used to sense the boundaries between Bare Kapton and recording medium.

An appropriate combination of photo sensors and read/write tape heads can be used to eliminate any possibility of indexing errors. The latter could cause the analytical results to be mismatched with the samples. Kapton tape with laser-engraved bar codes placed every 6 inches along the tape are adequate. A bar code reader is used to sense tape position and provide stop signals for bringing sample into proximity to the capillary tube.

The tape heater is retracted temporarily from the tape surface to prevent heating of the magnetic recording medium. Successive tape windings may be separated on the tape spools to prevent front-to-back transfer of samples between adjacent windings under some circumstances.

By placing the cassette tape into close proximity to the end of the capillary tube 260, vapors driven from the tape surface by heat are swept into the capillary tube and delivered to the interior of the mass spectrometer. Samples dispersed at roughly even intervals along the length of the cassette tape are wound to the heater probe tip, which is maintained at 300 degrees Centigrade. The samples vaporize rapidly from the tape surface, appearing as mass spectrometer signals which rise and fall in substantially less than one second. The response time of the system is sufficiently short, so that samples can analyzed in rapid succession by stepping the tape position from sample to sample. Throughput rates of 250 to 720 samples per hour are possible.

As can be understood from the above description, the invention has several advantages such as: (1) it permits off-line multiplexing of gas chromatographic and liquid chromatographic instruments to a single mass spectrometer; (2) it permits operation at or near atmospheric pressure; and (3) it permits the mass spectrometer to analyze samples as fast as samples can be advanced on the tape or as fast as the mass spectrometer can scan.

Firstly, off-line gas chromatographic and liquid chromatographic interfacing is obtained in combination with deposition means whereby liquid chromatographic or gas chromatographic effluents may be deposited upon the surface of the cassette tape.

With this mechanism, chromatograms can be mass analyzed at a higher rate of speed than the rate at which compounds elute from chromatographs. This comes about because the tape can be drawn across the capillary tube faster than it was drawn through the liquid chromatographic or gas chromatographic deposition region, and the mass spectrometer, owing to its inherent analysis speed, can keep up.

A single mass spectrometer (which costs ten times a typical gas chromatographic or liquid chromatographic) can support in real time, a number of gas chromatographs or liquid chromatographs equal to the ratio of average chromatographic elution time divided by average cassette analysis time. This ratio will range from 10 to 100 depending on the details of the analysis being performed. The end result is tenfold to hundredfold increase in the sample throughput rate of gas-chromatographic mass-spectrometer or liquid-chromatographic mass-chromatographic analysis, with no sacrifice in gas chromatographic or liquid chromatographic resolution.

Secondly, the cassette tape may be operated in a helium atmosphere at or near a pressure of 760 torr. It is unnecessary to draw the tape into the mass spectrometer through multistage differentially pumped vacuum locks (as in on-line belt interfaces), thus simplifying and reducing the cost over the prior art. This simplification is made possible by the "capillary tube" concept, or by the insertion of a probe between cassette reels which draws the tape mechanically through a standard vacuum lock into the vacuum chamber of a mass spectrometer.

Thirdly, it is well known that rapid heating of samples adsorbed to surfaces can cause certain compounds to become volatile, whereas, if the surface to which they are adsorbed is heated slowly, the same compounds decompose. The present invention provides new rapid heating means in that a local region of the cassette tape with neutral sample molecules adsorbed to its surface will heat very rapidly if, by virtue of appropriate winding motion at the cassette reels, the sample-bearing region of the tape is moved rapidly (less than one second) from a room temperature region to a hot region (e.g., 400 degrees Centigrade). This feature in combination with transfer tubes of suitable geometry may make possible the analysis of compounds normally considered nonvolatile. Rapid heating of the tape with a source of electromagnetic radiation may also be contemplated.

Although a preferred embodiment of the invention has been described with some particularity, many modifications and variations in the invention may be made without deviating from the invention. Accordingly, within the scope of the appended claims, the invention may be practiced other than as specifically described.

What is claimed is:

1. Apparatus comprising:
   a mass spectrometer;
   a transfer tube arrangement whereby one end of a capillary tube is adapted to communicate with a mass spectrometer so as to bring gaseous samples into close proximity to the mass spectrometer ionizing means and another end of the capillary tube is brought into close proximity to a surface of a cassette tape.

2. Apparatus according to claim 1 in which the one end of the capillary tube is adapter to communicate with a mass spectrometer interface.

3. Apparatus according to claim 1 in which the transfer tube arrangement is incorporated into a direct insertion probe and admitted to the mass spectrometer ionizing means through an ordinary vacuum lock.

4. Apparatus according to claim 1 further including means for moving the cassette tape across a heater such that a portion of the cassette tape having sample is moved from a low temperature region into a high temperature region at the heater tip in less than one second.

5. Apparatus according to claim 4 in which the cassette tape is operated at less than 2 atmospheres of pressure.

6. Apparatus according to claim 4 in which the cassette tape is locally heated only on those portions having sample.

7. Apparatus comprising:
   a mass spectometer;
   a cassette having a frame supporting two reels;
   a probe inserted through the cassette frame between the cassette reels to draw tape through a vacuum lock and into a mass spectrometer ion source, where samples would be driven from the tape surface directly into the mass spectrometer ion source either as neutrals or as ions, without the use of a carrier gas.

8. Apparatus comprising:
   a mass spectrometer;
   a cassette having a frame supporting two reels;
   said entire cassette structure being inserted into a mass spectrometer ion source through a suitably designed vacuum lock.

9. Apparatus comprising:
   a mass spectrometer;
   a transfer tube arrangement whereby one end of a capillary tube is affixed directly to a vacuum chamber of the mass spectrometer so as to bring effluent into a mass spectrometer, and another end of the capillary tube is brought into close proximity to a surface of a cassette tape;
   an ionizing means, located between the cassette tape and a location near the input end of the transfer tube arrangement for causing sample molecules to become ionized and be carried through the transfer tube arrangement in ionized form by a carrier gas into the mass spectrometer, whereby the transfer tube arrangement serves as an ion source as well as a sample transport means.

10. Apparatus according to claim 9, wherein said ionizing means is incorporated into the body of the transfer tube arrangement.

11. Apparatus according to claim 9, wherein said ionizing means is near the exit of the capillary tube such that sample molecules traveling through the capillary tube may be ionized just prior to exiting from the capillary tube, so that the cassette interface performs the function of an ion source.

12. Apparatus according to claim 9, wherein the ionizing means is located near the entrance of the transfer tube arrangement between the cassette tape and the transfer tube arrangement for causing sample molecules to become ionized and be carried through the transfer tube arrangement by the carrier gas into the mass spectrometer, whereby the cassette tape serves as an ion source as well as a sample transport means.

13. Apparatus according to claim 9, wherein carrier gas is mixed with reagent gas so as to achieve chemical ionization of sample molecules.

14. Transfer means comprising a capillary tube having one end placed in proximity to a sample injector and another end of the capillary tube in proximity to an analyzing section of an analytical instrument; means for heating the capillary tube whereby samples are maintained in gaseous form; and including the surface of a cassette tape and means for heating the cassette tape.

15. Transfer means comprising:
   a cassette having a frame supporting two reels;
   a probe inserted through the cassette frame between the cassette reels to draw tape through a seals and into an analytical instrument, where samples are driven from the tape surface.

16. Transfer means according to claim 15 further including heater means for increasing the heat of the tape and means for moving a portion of the tape including a sample into contact with the heating means.

17. Transfer means according to claim 16 in which the tape includes adsorbing means having sample on it.

18. Transfer means according to claim 16 in which the tape includes:
   rapid gasification means having a predetermined temperature of gasification;
   said rapid gasification means including sample in the rapid gasification means; and
   said means for heating including means for heating to said predetermined temperature for rapid gasification.

19. A method of injecting samples into an instrument comprising the steps of:
   drawing tape out of a cassette structure by means of a probe inserted through a cassette frame between reels of the cassette;
   moving sample rapidly from a low temperature region to a high temperature sampling region; and
   vaporizing sample from the tape.

20. A method according to claim 19 further comprising the step of locating sample and controlling tape movement by means of bar codes on the tape surface.

21. A method comprising the steps of:
   ionizing sample molecules during a time period occuring from prior to through its transport through a transfer tube; and
   transporting sample ions through a capillary transfer tube to a mass spectrometer in such manner that a cassette structure, equipped with ionizing means, functions as an ion source of the mass spectrometer.

22. A method comprising the steps of doping a carrier gas with reagent gas such that chemical ionization of samples may take place within in a location including at least a portion of a path through the body of a transfer tube and an area within a gap between an entrance of a transfer tube and a cassette tape surface.

23. A cassette tape comprising tape means having sample deposition areas and data markings spaced alternately along the length of the tape.

24. A cassette tape according to claim 23 wherein the data markings comprise magnetic data recording medium.

25. A method of injecting samples into an instrument comprising the steps of:
   depositing sample at spaced apart locations on a tape;
   marking the tape between samples with a code indicating at least one characteristic of the sample;
   moving tape in a cassette into a sample region; and
   vaporizing sample from the tape for injection into the instrument.

26. A method according to claim 25 in which said step of marking the tape includes the step of recording data pertinent to a particular sample on magnetic recording medium located on the tape in proximity to the sample.

27. A method of transferring sample into an analytical instrument comprising the steps of:
   vaporizing sample from the surface of a cassette tape or rotatable disk;
   injecting sample so vaporized into one end of a capillary tube;
   injecting carrier gas with the vaporized sample;
   moving the carrier gas and vaporized sample into the analytical instrument by viscous flow.

* * * * *